United States Patent [19]

Ichikawa et al.

[11] Patent Number: 5,348,890

[45] Date of Patent: Sep. 20, 1994

[54] TRIOXANE DERIVATIVES, AND METHOD FOR THE CHEMILUMINESCENCE

[75] Inventors: Shuji Ichikawa; Motohiro Mitani; Yuko Yokoyama, all of Ibaraki; Hideo Sawada, Kanagawa; Takeo Matsumoto, Ibaraki, all of Japan

[73] Assignee: NOF Corporation, Japan

[21] Appl. No.: 986,040

[22] Filed: Dec. 4, 1992

[30] Foreign Application Priority Data

Dec. 4, 1991 [JP] Japan .................. 3-347761
Mar. 31, 1992 [JP] Japan .................. 4-104005

[51] Int. Cl.$^5$ .............. G01N 21/76; C07D 323/04
[52] U.S. Cl. ........................ 436/172; 549/367; 436/100
[58] Field of Search .............. 549/367; 436/172, 100

[56] References Cited

PUBLICATIONS

Yamamoto et al. "Synthesis and Reactions of 5-Arylamino 1,2,4 trioxans" JCS Perkin I, 1980. pp. 2300–2303.

Nakamura et al. "Synthesis and Chemiluminescence of [5(2 Pyridyl), (2-pyrazimyl)-,and Substituted 2 Pyrazinyl)amino] 1,2,4 trioxanes" Bull Chem. Soc. Jpn. vol. 61, No. 10 pp. 3776–3778 (1988).

Teranishi et al., "No Electron Donating Substituent Effect on The Singlet Excited State Formation from the 5 (5 Aryl 2-Pyrazinylamino) 1,2,4 trioxanes" Bull Chem. Soc. Jpn vol. 62 pp. 2009–2012 (1989).

Jefford et al., "New Chemistry of Zwitterionic Peroxides arising by Photooxidation of enol ethers" Tetrahedron vol. 41 No. 11 pp. 2081–2088 (1985).

Primary Examiner—James C. Housel
Assistant Examiner—Jan M. Ludlow
Attorney, Agent, or Firm—Wenderoth, Lind & Ponack

[57] ABSTRACT

Trioxane derivatives represented by the formula (I):

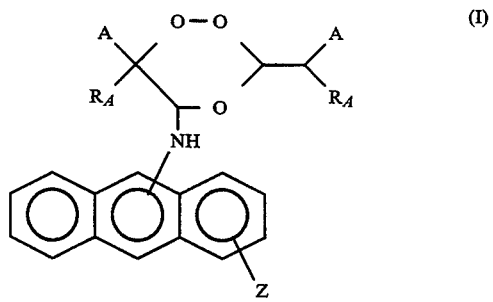

wherein A and $R_A$ are the same with or different from each other, and represent a substituted or unsubstituted aliphatic hydrocarbon group, respectively, or represent $R_1$—$X_1$— or $R_2$—$X_2$— in which $X_1$ and $X_2$ represent independently a divalent organic residue, and $R_1$ and $R_2$ represent independently carboxyl group, amino group, hydroxyl group or mercapto group, and Z represents hydrogen atom, halogen atom, methyl group, ethyl group or propyl group, or carboxyl, amino, hydroxyl or mercapto group through a divalent organic residue, and process for the preparation thereof, as well as method for chemiluminescence comprising mixing the trioxane derivatives and a base.

4 Claims, No Drawings

TRIOXANE DERIVATIVES, AND METHOD FOR THE CHEMILUMINESCENCE

FIELD OF THE INVENTION

This invention relates to novel trioxane derivatives, a process for the preparation thereof and a method for the chemiluminescence. The derivatives according to this invention are used for a detection agent for various diagnostics and an emergency source of light, and the like.

BACKGROUND OF THE INVENTION

The chemiluminescence is meant for a phenomenon wherein an atom or molecule is excited with energy produced by chemical reaction to emit light. Up to the present time, many substances having various chemical skeletons have been developed as the chemiluminescence compounds, and there are known acridinium esters, oxalic acid esters and the like. These compounds are used for detection agent for diagnostics or an emergent source of light.

There are well known reactions, for example, by luminol which is famous in identification of bloodstain, lucigenin [bis(N-methylacridinium nitrate)], lophine (2,4,5-triphenyl-imidazole) or gallic acid, and the like.

These compounds emit a light in the presence of hydrogen peroxide and a metal such as Fe under an alkaline condition. The atom or molecule participating in the reaction can be determined quantitatively by detecting the light generated herein by means of a photomultiplier tube. Many of compounds such as vitamin $B_{12}$, glucose and the like have been determined.

Further, there is known as another prior art a luminescence system wherein an active intermediate produced by the reaction of an oxalic acid ester with hydrogen peroxide excites a fluorescent material to make it luminescent. There is established a method for determining an original amount of glucose by determining quantitatively, by the use of this prior art, hydrogen peroxide generated from glucose by the action of glucose oxidase.

On the other hand, it is known that 5-(9-anthrylamino)-3-isopropyl-6,6-dimethyl-1,2,4-trioxane having a trioxane skeleton has an ability of chemiluminescence, too. The feature of the luminescence thereof is that luminescent wave length of the anthrylaminotrioxane is over than 500 nm, while the luminescent wave length of acridinium ester, luminol etc. are less than 500 nm (J.C.S. Chem. Comn., 180,, 1976). Therefore, even if a protein or nucleic acid coexists, it is hardly affected.

However, such prior trioxane compounds have a drawback that they are disadvantageous to the application for analysis wherein accuracy is required, since they luminesce only in an anhydrous or aprotic solvent. Accordingly, it is a fact that there is strongly desired the development of trioxane derivatives that the chemiluminescence is observed in an aqueous solvent.

SUMMARY OF THE INVENTION

An object of this invention is to provide novel trioxane derivatives having a substituent which is capable of bonding protein, nucleic acid, etc., and having almost the same level of quantity of light of luminescence in an organic solvent as in an aqueous solvent.

Another object of this invention is to provide a process for preparing novel trioxane derivatives having a substituent which is capable of bonding protein, nucleic acid, etc., and having almost the same level of quantity of light of luminescence in an aqueous solvent as in an organic solvent.

Further object of this invention is to provide a method for the chemiluminescence, characterized by mixing the novel trioxane derivative of this invention and a base to effect a chemiluminescence.

Still another object of this invention is to provide a kit comprising a combination of the novel trioxane derivative of this invention and a base, that is, so-called "a kit product". According to the kit product of this invention, the chemiluminescence can be effected by mixing in situ the novel trioxane derivative and a base.

Still further object of this invention is to establish a method for quantitative determination of an atom or molecule participating in the reaction, by the use of the chemiluminescence reaction by virtue of the novel trioxane derivative of this invention, thereby enlarging the application of the trioxane derivatives.

DETAILED DESCRIPTION OF THE INVENTION

The following are the aspects of the present invention.

1. Trioxane derivatives represented by the formula (I):

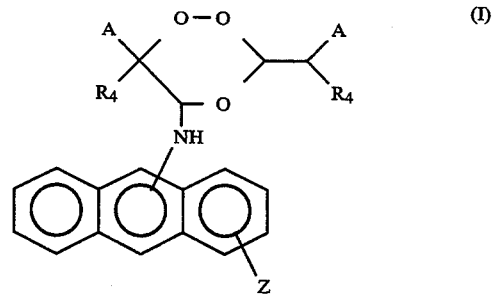

wherein A and RA are the same with or different from each other, and represent a substituted or unsubstituted aliphatic hydrocarbon group having one to three carbon atoms respectively, or represent $R_1—X_1—$ or $R_2—X_2—$ in which $X_1$ and $X_2$ represent independently a divalent organic residue, and $R_1$ and $R_2$ represent independently carboxyl group, amino group, hydroxyl group or mercapto group; and Z represents hydrogen atom, halogen atom, methyl group, ethyl group or propyl group, or carboxyl, amino, hydroxyl or mercapto group through a divalent organic residue with the exception that A and RA represent methyl group, and Z represents hydrogen atom.

2. Trioxane derivatives as set forth in the aspect 1, represented by the formula (II):

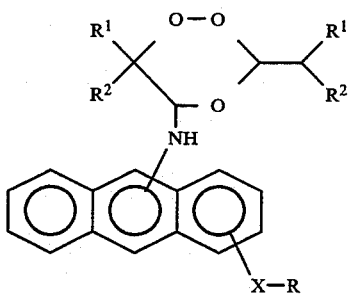
(II)

wherein X represents a divalent organic residue, R represents carboxyl group, amino group, hydroxyl group or mercapto group, and $R^1$ and $R^2$ are the same or different and represent a substituted or unsubstituted aliphatic hydrocarbon group having one to three carbon atoms respectively, with the exception that $R^1$ and $R^2$ represent methyl group, and R—X—represents hydrogen atom.

3. Trioxane derivatives as set forth in the aspect 1 represented by the formula (III):

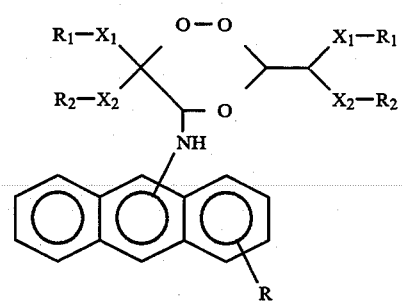
(III)

wherein $X_1$ and $X_2$ represent independently a divalent organic residue, and $R_1$ and $R_2$ represent independently carboxyl group, amino group, hydroxyl group or mercapto group; $R_2$—$X_2$—may be methyl group, ethyl group or propyl group; and R represents hydrogen atom, halogen atom, methyl group, ethyl group or propyl group.

4. A process for preparing trioxane derivatives represented by the formula (I):

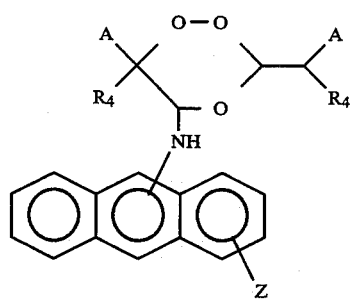
(I)

wherein A and RA are the same with or different from each other, and represent a substituted or unsubstituted aliphatic hydrocarbon group having one to three carbon atoms respectively, or represent $R_1$—$X_1$— or $R_2$—$X_2$—in which $X_1$ and $X_2$ represent independently a divalent organic residue, and $R_1$ and $R_2$ represent independently carboxyl group, amino group, hydroxyl group or mercapto group; and Z represents hydrogen atom, halogen atom, methyl group, ethyl group or propyl group, or carboxyl, amino, hydroxyl or mercapto group through a divalent organic residue with the exception that A and RA represent methyl group, and Z represents hydrogen atom, which comprises reacting an anthrylamine derivative represented by the formula (IV):

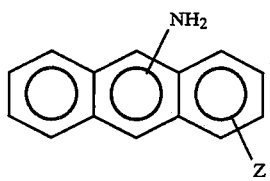
(IV)

wherein Z represents hydrogen atom, halogen atom, methyl group, ethyl group or propyl group; or carboxyl group, protected carboxyl group, protected amino group, hydroxyl group, protected hydroxyl group, or protected mercapto group, with an aldehyde derivative represented by the formula (V):

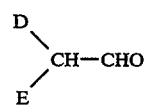
(V)

wherein D and E are the same or different, and represent a substituted or unsubstituted aliphatic hydrocarbon group having from one to three carbon atoms respectively, or represent $R_3$—$X_1$—or $R_4$—$X_2$—in which $X_1$ and $X_2$ represent independently a divalent organic residue, and $R_3$ and $R_4$ represent independently protected carboxyl group, protected amino group, protected hydroxyl group or protected mercapto group, and $R_4$—$X_2$—may be methyl group, ethyl group or propyl group, and an oxygen, followed by, if necessary, subjecting it to a deprotection.

5. A process for preparing trioxane derivatives as set forth in the aspect 4, represented by the formula (II):

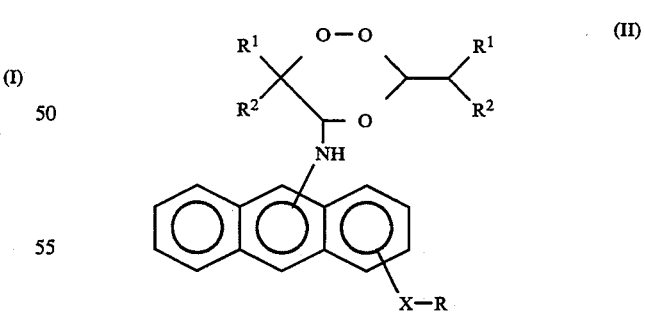
(II)

wherein X represents a divalent organic residue, R represents carboxyl group, amino group, hydroxyl group or mercapto group, and $R^1$ and $R^2$ are the same or different, and represent a substituted or unsubstituted aliphatic hydrocarbon group having one to three carbon atoms, respectively, with the exception that $R^1$ and $R^2$ represent methyl group, and R—X—represents hydrogen atom, which comprises reacting an anthrylamine derivative represented by the formula (VI):

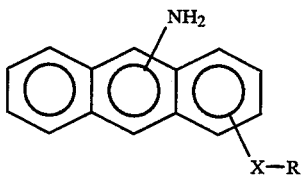

wherein X represents a divalent organic residue, and R represents carboxyl group, protected carboxyl group, protected amino group, hydroxyl group, protected hydroxyl group or protected mercapto group, with an aliphatic aldehyde derivative represented by the formula (VII):

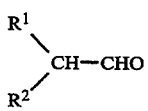

wherein $R^1$ and $R^2$ have the same meanings as defined above, and an oxygen, if necessary, followed by subjecting it to a deprotection.

6. A process for preparing trioxane derivatives as set forth in the aspect 4, represented by the formula (III):

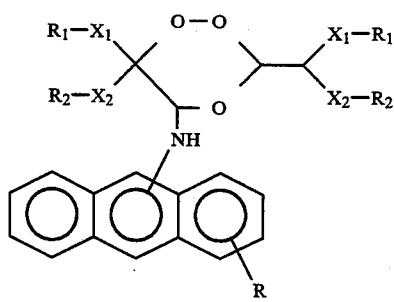

wherein $X_1$ and $X_2$ represent independently a divalent organic residue, and $R_1$ and $R_2$ represent independently carboxyl group, amino group, hydroxyl group or mercapto group; $R_2-X_2-$ may be methyl group, ethyl group or propyl group; and R represents hydrogen atom, halogen atom, methyl group, ethyl group or propyl group, which comprises reacting an anthrylamine derivative represented by the formula (VIII):

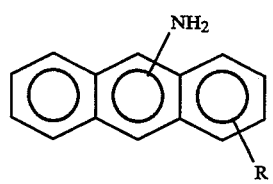

wherein R has the same meanings as defined above, with an aldehyde derivative represented by the formula (IX):

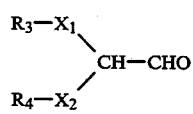

wherein $X_1$ and $X_2$ represent a divalent organic residue, and $R_3$ and $R_4$ represent independently protected carboxyl group, protected amino group, protected hydroxyl group or protected mercapto group; $R_4-X_2-$ may be methyl group, ethyl group or propyl group; and an oxygen, followed by subjecting it to a deprotection.

7. A method for chemiluminescence, characterized in that the chemiluminescence is effected by mixing trioxane derivative represented by the formula (I):

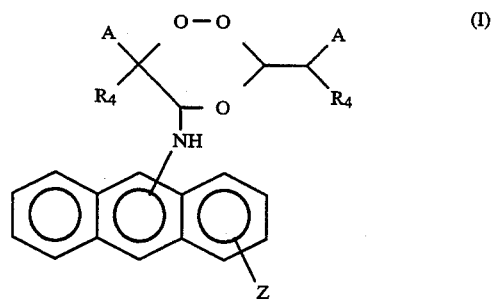

wherein A and RA are the same with or different from each other, and represent a substituted or unsubstituted aliphatic hydrocarbon group having one to three carbon atoms respectively, or represent $R_1-X_1-$or $R_2-X_2-$in which $X_1$ and $X_2$ represent independently a divalent organic residue, and $R_1$ and $R_2$ represent independently carboxyl group, amino group, hydroxyl group or mercapto group; and Z represents hydrogen atom, halogen atom, methyl group, ethyl group or propyl group, or a carboxyl, amino, hydroxyl or mercapto group through a divalent organic residue with the exception that A and RA represent methyl group, and Z represents hydrogen atom, and a base.

8. A kit comprising a combination of a trioxane derivative represented by the formula (I):

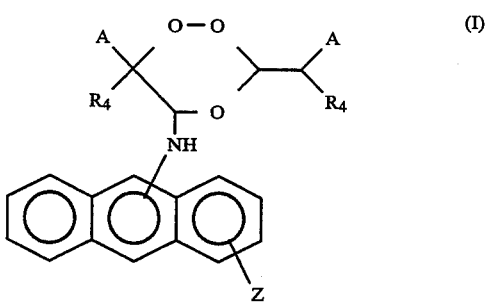

wherein A and RA are the same with or different from each other, and represent a substituted or unsubstituted aliphatic hydrocarbon group having one to three carbon atoms respectively, or represent $R_1-X_1-$or $R_2-X_2-$in which $X_1$ and $X_2$ represent independently a divalent organic residue, and $R_1$ and $R_2$ represent independently carboxyl group, amino group, hydroxyl group or mercapto group; and Z represents hydrogen atom, halogen atom, methyl group, ethyl group or propyl group, or a carboxyl, amino, hydroxyl or mercapto group through a divalent organic residue with the exception that A and RA represent methyl group, and Z represents hydrogen atom, and a base.

This invention is described more in detail as follows.

In the novel trioxane derivatives of this invention represented by the formula (II), for example, 5-(9- anthrylamino)-3-isopropyl-6,6-dimethyl-1,2,4-trioxane derivative, 5-(1-anthrylamino)-3-isopropyl-6,6-dimethyl-1,2,4-trioxane derivative, 5-(2-anthrylamino)-3-isopropyl-6,6-dimethyl-1,2,4-trioxane derivative and the like, X is a divalent organic residue exemplified by:

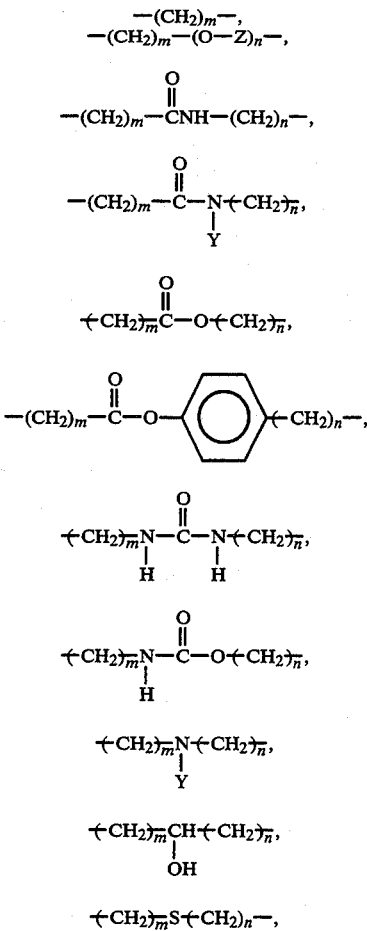

wherein m and n represent an integer from 1 to 10, Y represents a lower alkyl group and Z represents a lower alkylene group, for example, $C_{1-3}$ alkylene group.

In the formula (II), R represents carboxyl group, amino group, hydroxyl group or mercapto group. Accordingly, —X—R is, for example, 2-carboxyethyl, 2-(2-aminoethoxy)ethyl, 4-[N-(2-hydroxyethyl)carbamoyl]butyl, 3-mercaptopropyl and the like.

In the formula (II), $R^1$ and $R^2$ are the same or different representing a substituted or unsubstituted lower aliphatic hydrocarbon group having from 1 to 3 carbon atoms, for example, methyl group, ethyl group, n-propyl group and the like and substituted group thereof, respectively.

The most preferable aldehyde represented by the formula (VII) is isobutyraldehyde wherein both $R^1$ and $R^2$ are represented by methyl group.

The anthrylamine derivatives represented by the formula (VI) are exemplified as follows:
10-(2-carboxyethyl)-9-anthrylamine,
10-(1-carboxymethyl)-1-anthrylamine,
10-(3-carboxypropyl)-2-anthrylamine,
2-(4-carboxybutyl)-9-anthrylamine,
10-[2-(2-aminoethoxy)ethyl]-9-anthrylamine,
3-[2-(4-aminobutoxy)ethyl]-1-anthrylamine,
4-[2-(2-aminobutoxy)ethyl]-2-anthrylamine,
10-[4-[N-(2-hydroxyethyl)carbamoyl]-9-anthrylamine, and
10-(3-mercaptopropyl)-9-anthrylamine.

The procedures and conditions for preparing novel trioxane derivatives (formula II) according to this invention can be broadly varied. An amount of the starting materials of this invention represented by the formula (VI) and the formula (VII) can be varied in a range of from about 1:2 to about 1:1000, preferably from about 1:3 to about 1:100 in a mole ratio of the anthrylamine derivative represented by the formula (VI) to the aldehyde derivative represented by the formula (VII).

Reaction temperature employed in this invention may usually be a room temperature, but the target material can be optionally obtained with a good yield in a short time by subjecting the reaction to a heating under reflux for several hours, followed by the reaction at a room temperature.

The reaction in this invention is effected in an inert solvent. Any various solvents can be used with the proviso that the solvents are inert under the reaction condition and easily separated from the trioxane derivatives produced. As especially suitable solvent, there may be mentioned ether, dimethoxyethane, tetrahydrofuran, hexane, benzene or a mixed solvent thereof. Amount of the solvent used is not critically limited, but it can be varied in a range of from about 0.5 times to about 100 times on the basis of the total weight of the starting materials.

The reaction of the anthrylamine derivative represented by the formula (VI) with the aldehyde derivative represented by the formula (VII) and an oxygen according to this invention is effected usually under atmospheric pressure, but can be effected also under super-atmospheric pressure or sub-atmospheric pressure depending on other reaction conditions, the materials used, desired rate of reaction, etc. An oxygen to be used may contain other inert gases. It is especially preferable to use an air free from moisture.

The reaction in this invention is effected for a sufficient time to produce a crude product of trioxane derivative. The exact reaction time is determined depending on reaction temperature, reaction pressure, ratio of amount of the starting materials, etc., and it is usually in a range from about one hour to about 14 days, and preferably from about 10 hours to about 7 days.

The crude product of trioxane derivative produced is dissolved in a proper solvent such as acetone etc., or a mixture thereof, followed by deposition as crystal by conventional manner.

With respect to the novel trioxane derivatives of this invention represented by the formula (III), $R_1$ and $R_2$ represent independently carboxyl group, amino group, hydroxyl group or mercapto group, and they are substituents capable of bonding with protein, nucleic acid, etc.

Accordingly —$X_1$—$R_1$, —$X_2$—$R_2$ are, for example, 5-carboxypentyl, 4-(2-aminoethoxy)butyl, 4-[N-(2-hydroxyethyl)carbamoyl]butyl, and the like.

$X_2$—$R_2$ also may be methyl group, ethyl group or propyl group.

In the formula (III), R may be hydrogen atom, chlorine atom, bromine atom, iodine atom, fluorine atom, methyl group, ethyl group or propyl group.

The most preferable anthrylamine derivative represented by the formula (VIII) is 9-anthrylamine wherein R is hydrogen atom.

In the formula (IX), the protective groups of $R_3$ and $R_4$ are used for the purpose to inhibit side reactions in the reaction with an anthrylamine represented by the formula (VIII). As these protective groups, there can be used t-butyldimethylsilyl group, t-butyldiphenylsilyl group, 2-trimethylsilylethoxycarbonyl group, benzyloxycarbonyl group, acetyl group, trifluoroacetyl group, etc.

Examples of the $R_3$ and $R_4$ are concretely t-butyldimethylsiloxycarbonyl group, t-butyldiphenylsiloxycarbonyl group, 2-trimethylsilylethoxycarbonylamino group, benzyloxycarbonylamino group, t-butyldimethylsiloxy group, t-butyldiphenylsiloxy group, s-acetylmercapto group, s-trifluoroacetylmercapto group, etc.

Exemplified aldehydes represented by the formula (IX) include the followings:
- 2-methyl-7-(t-butyldimethylsiloxycarbonyl)heptanal,
- 2-methyl-5-(t-butyldimethylsiloxycarbonyl)pentanal,
- 2-methyl-9-(2-trimethylsilylethoxycarbonylaminoethoxy)-7-oxanonanal,
- 2-ethyl-6-(2-trimethylsilylethoxycarbonyl)aminohexanal,
- bis-[4-[N-[2-(t-butyldimethylsiloxy)ethyl]carbamoyl]butyl]acetaldehyde,
- bis-[3-(t-butyldimethylsiloxy)propyl]acetaldehyde,
- 2-methyl-15-(t-butyldimethylsiloxy)-7,10,13-trioxapentadecanal,
- 2-methyl-6-(s-acetylmethylmercapto)hexanal.

Broad variations may be possible with respect to the means, conditions etc. of reaction to produce the novel trioxane derivatives of this invention according to this invention, from an anthrylamine derivative represented by the formula (VIII), an aldehyde derivative represented by the formula and an oxygen.

The amount of the starting materials used in this invention represented by the formula (VIII) and the formula (IX) can be varied in a range of from about 1:2 to about 1:1000, preferably from about 1:3 to about 1:100 in the mole ratio of the anthrylamine derivative represented by the formula (VIII) to the aldehyde derivative represented by the formula (IX). This is the same as in the starting materials of this invention represented by the formulae (VI) and (VII).

With respect to reaction temperature, reaction pressure, reaction time, and solvent as well as purification procedure, the same considerations are applicable.

For removing the protective group on the protected trioxane derivatives, it is appropriate to effect a treatment by tetrabutyl ammonium fluoride, cesium fluoride, potassium carbonate or sodium carbonate.

In the method for the chemiluminescence according to this invention, the chemiluminescence phenomenon is caused not only in an organic solvent but also in an aqueous system. Base is generally preferable to be water soluble and, there are mentioned, for example, potassium t-butoxide, sodium hydroxide, potassium hydroxide, potassium carbonate, sodium carbonate, sodium hydrogencarbonate, tetrabutylammonium hydroxide and the like.

In the method for the chemiluminescence according to this invention, the chemiluminescence is also caused by mixing an organic solvent in addition to the trioxane derivative of this invention and base. In such a case, it is preferable to use an organic solvent, for example, a polar solvent. Suitable solvents are dimethyl sulfoxide, dimethylformamide, HMPA, dioxane, acetonitrile, methyl alcohol, ethyl alcohol, t-butyl alcohol or nitromethane.

This invention is explained more concretely by the following examples and comparative examples. In Examples 1–4 and 6–9, IR absorption spectrum data by IR-810 made by Nihon Bunko Co., Ltd. in Japan and mass spectrometric analysis data by DX-303 made by JOEL Ltd. in Japan are described in this order as the data to identify the target trioxane derivatives. In Examples 5 and 10 as well as Comparative Examples 1 and 2, there are noted count numbers measured for the amount of chemiluminescence using BLX-201 made by Aloka Co. in Japan.

Example 1

Synthesis of 5-[9-[10-(2-carboxyethyl)anthryl]amino]-3-isopropyl-6,6-dimethyl-1,2,4-trioxane represented by the structural formula (X):

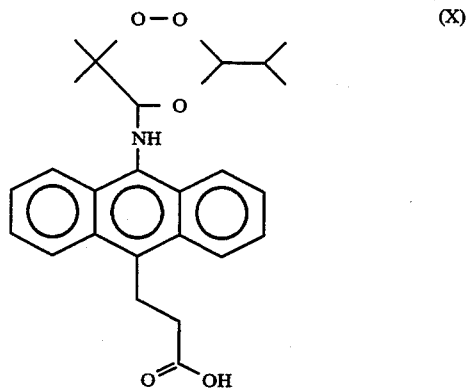

Under moisture-free air atmosphere, 612 mg(2.31 mmol) of 9-[10-(2-carboxyethyl)anthryl]amine were added to a mixed solution of 7 ml of isobutyraldehyde and 28 ml of ethyl ether, and the mixture was stirred for a week in a dark room at room temperature. The reaction liquid was concentrated under reduced pressure. The residue produced was recrystallized from an ether-hexane mixed solvent to produce 891 mg (2.10 mmol) of 5-[9-[10-(2-carboxyethyl)anthryl]amino]-3-isopropyl-6,6-dimethyl-1,2,4-trioxane.

IR (KBr) $cm^{-1}$ 3370 (H—N), 3000 (H—OOC), 1705 (O=COH), 1610 (C=C).

MS m/z 423 (M+)

| Elemental analysis ($C_{25}H_{29}NO_5$) | | | |
|---|---|---|---|
| | C | H | N |
| Calculated (%) | 70.90 | 6.90 | 3.31 |
| Found (%) | 70.71 | 6.99 | 3.40 |

Example 2

Synthesis of 5-[9-[10-[2-(2-aminoethoxy)ethyl]anthryl]amino]-3-isopropyl-6,6-dimethyl-1,2,4-trioxane represented by the structural formula (XI):

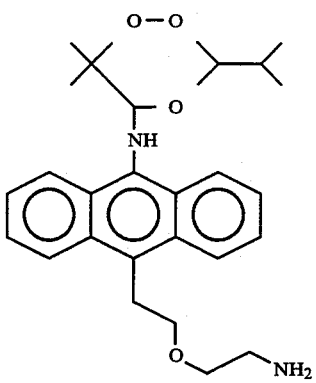

(XI)

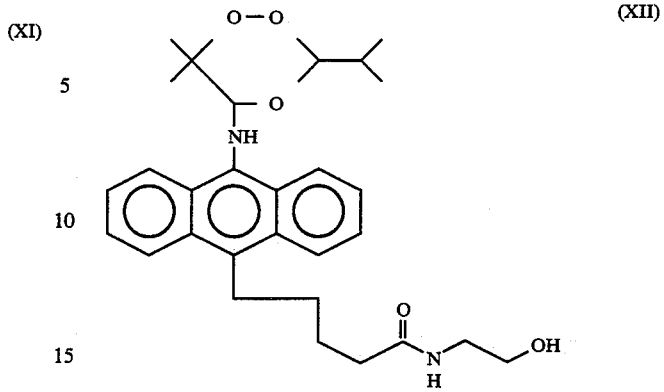

(XII)

Under moisture-free air atmosphere, 1.90 g (4.58 mmol) of 9-[10-[2-(2-benzyloxycarbonylaminoethoxy)ethyl]anthryl]amine were added to a mixed solution of 4 ml of isobutyraldehyde and 16 ml of hexane and the mixture was stirred for a week in a dark room at a room temperature. The reaction liquid was concentrated under reduced pressure, and the residue produced was subjected to silica gel column chromatography. The residue was developed with hexane-ether (50:1) as an eluate to produce 1.91 g (3.34 mmol) of 5-[9-[10-[2-(2-benzyloxycarbonylaminoethoxy)ethyl]anthryl]amino]-3-isopropyl-6,6-dimethyl-1,2,4-trioxane.

To a solution of 1.91 g (3.34 mmol) of said compound in 25 ml of dimethoxyethane were added 125 mg of 5% palladium carbon. The mixture was stirred for an hour under hydrogen atmosphere. Thereafter, the reaction liquid from which insolubles are removed by filtration was concentrated under reduced pressure. The residue produced was recrystallized from ether-hexane to produce 1.32 g (3.01 mmol) of 5-[9-[10-[2-(2-aminoethoxy)ethyl]anthryl]amino]-3-isopropyl-6,6-dimethyl-1,2,4-trioxane.

IR (KBr) cm$^{-1}$ 3380, 3300 (H—N, H$_2$N), 1605 (C=C)

MS m/z 438 (M$^+$)

| Elemental analysis (C$_{26}$H$_{34}$N$_2$O$_4$) | | | |
|---|---|---|---|
| | C | H | N |
| Calculated (%) | 71.21 | 7.81 | 6.39 |
| Found (%) | 71.49 | 7.70 | 6.51 |

Example 3

Synthesis of 5-[9-[10-[4-[N-(2-hydroxyethyl)carbamoyl]butyl]anthryl]amino]-3-isopropyl-6,6-dimethyl-1,2,4-trioxane represented by the structural formula (XII):

Under moisture-free air atmosphere, 962 mg (2.86 mmol) of 9-[10-[4-[N-(2-hydroxyethyl)carbamoyl]butyl]anthyryl]amine were added to a mixed solution of 2 ml of isobutyraldehyde, 2 ml of dimethoxyethane and 10 ml of hexane, and the mixture was stirred for a week in a dark room at a room temperature. The reaction liquid was concentrated under reduced pressure, and the residue produced was recrystallized from ether-hexane to produce 1.14 g (2.55 mmol) of 5-[9-[10-[4-[N-(2-hydroxyethyl)carbamoyl]butyl]anthryl]amino]-3-isopropyl-6,6-dimethyl-1,2,4-trioxane.

IR (KBr) cm$^{-1}$ 3380, 3300 (H—N, H—O), 1660 (O=C), 1610 (C=C)

MS m/z 494 (M$^+$)

| Elemental analysis (C$_{29}$H$_{38}$N$_2$O$_5$) | | | |
|---|---|---|---|
| | C | H | N |
| Calculated (%) | 70.42 | 7.74 | 5.66 |
| Found (%) | 70.70 | 7.82 | 5.57 |

Example 4

Synthesis of 5-[9-[4-(3-mercaptopropyl)anthryl]amino]-3-isopropyl-6,6-dimethyl-1,2,4-trioxane represented by the structural formula (XIII):

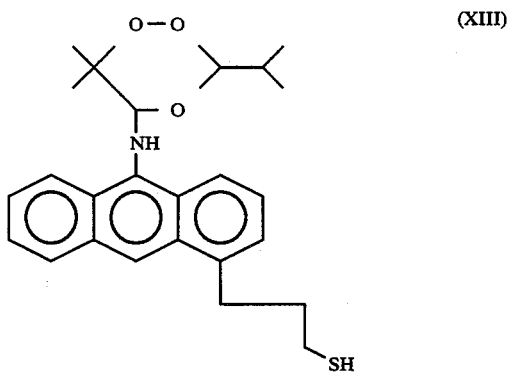

(XIII)

Under moisture-free air atmosphere, 2.02 g (5.63 mmol) of 9-[4-[3-(S-acetylmercapto)propyl]anthryl]amine were added to a mixed solution of 1.8 ml of isobutyraldehyde, 2 ml of diethylether and 10 ml of hexane and the mixture was stirred for one week in a dark room at a room temperature. The reaction liquid was concentrated under reduced pressure, and the residue produced was recrystallized from ether-hexane to produce 2.81 g (6.01 mmol) of 5-[9-[4-[3-(S-acetylmercapto)- propyl]anthryl]amino]-3-isopropyl-6,6-dimethyl-1,2,4-trioxane.

To a solution of 2.81 g (6.01 mmol) of said compound in 56 ml of methanol were added at 0° C. 831 mg (6.01 mmol) of potassium carbonate, and the mixture was stirred for 10 minutes. The reaction liquid was subjected to ether-water extraction and the organic layer was concentrated under reduced pressure. The residue produced was recrystallized from ether-hexane to produce 2.07 g (4.86 mmol) of 5-[9-[4-(3-mercaptopropyl)anthryl]amino]-3-isopropyl-6,6-dimethyl-1,2,4-trioxane.

IR (KBr) cm$^{-1}$ 3380 (H—N), 1610 (C=C)
MS m/z 425 (M+)

| Elemental analysis (C$_{25}$H$_{31}$NO$_3$S) | | | |
|---|---|---|---|
| | C | H | N |
| Calculated (%) | 70.55 | 7.34 | 3.29 |
| Found (%) | 80.73 | 7.22 | 3.38 |

Example 5

A 100 µl solution of dimethylsulfoxide containing 10$^{-3}$M of 5-[9-[10-(2-carboxyethyl)anthryl]amino]-3-isopropyl-6,6-dimethyl-1,2,4-trioxane synthesized in Example 1 as a measuring compound was injected into a cell containing 900 µl of a solvent containing a base in an equipment for measuring chemiluminescence and immediately thereafter an amount of luminescence for 10 seconds was measured. In that case, there were used a solution of potassium t-butoxide in 0.05M dimethylsulfoxide as an organic solvent containing a base, and a 10M aqueous solution of sodium hydroxide as an aqueous solvent, respectively. The results of measurement are shown in Table 1. The measured count numbers in Table 1 are "no unit" relative values.

Comparative Example 1

The same experiment for the measurement as in Example 5 was carried out using 5-(9-anthrylamino)-3-isopropyl-6,6-dimethyl-1,2,4-trioxane in place of 5-[9-[10-(2-carboxyethyl)anthryl]amino]-3-isopropyl-6,6-dimethyl-1,2,4-trioxane in Example 5. The results are shown in Table 1. The measured count numbers in Table 1 are "no unit" relative values.

TABLE 1

| | Organic solvent | Aqueous Solvent |
|---|---|---|
| Example 5 | 2.65 × 10$^5$ | 1.97 × 10$^5$ |
| Comparative Example 1 | 2.14 × 10$^5$ | 5.31 × 10$^3$ |

Example 6

Synthesis of 3-(1-methyl-6-carboxyhexy)-5-(9-anthrylamino)-6-methyl-6-(5-carboxypentyl)-1,2,4-trioxane expressed by the structural formula (XIV)

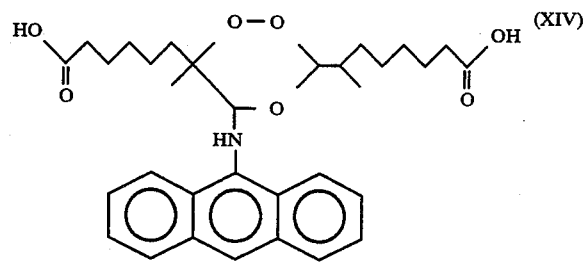

Under an argon atmosphere, 1.14 g (5.90 mmol) of 9-anthrylamine was added to a solution of hexane (11 ml) containing 5.09 g (17.8 mmol) of 2-methyl-7-(t-butyldimethylsiloxycarbonyl) heptanal, and the resulting mixture was agitated at room temperature in a dark room overnight to effect a reaction, followed by subjecting the mixture to the reaction for one week in a moisture-free air atmosphere. The reaction liquid was concentrated under reduced pressure, and the resulting residue was subjected to a silica gel column chromatography. By developing the same residue with hexane—ether (50:1) as an eluate, 3.85 g (4.93 mmol) of 3-[1-methyl-6-(t-butyl-dimethylsiloxycarbonyl) hexyl]-5-(9-anthrylamino)-6-methyl-6-[5-(t-butyldimethylsiloxycarbonyl) pentyl]-1,2,4-trioxane were obtained.

Into a solution of tetrahydrofuran (77 ml) containing 3.85 g (4.93 mmol) of the above-mentioned compound was added a solution of tetrahydrofuran [9.86 ml (9.86 mmol)] containing 1.0 M of tetrabutylammonium fluoride, and the resulting mixture was agitated overnight. Then a residue obtained by concentrating the reaction liquid under reduced pressure was subjected to an ethyl acetate—water extraction procedure, and its organic layer was concentrated under reduced pressure. The resulting residue was recrystallized in dichloromethane—hexane, thereby obtaining 2.56 g (4.64 mmol) of 3-(1-methyl-6-carboxyhexyl)-5-(9-anthrylamino)6-methyl-6-(5-carboxypentyl)-1,2,4-trioxane.

IR (KBr)cm$^{-1}$ :3,380 (H—N), 3,000 (H—OOC), 1,710 (O=COH) and 1,610 (C=C)
MS m/z : 551 (M+)

| Elemental Analysis (C$_{32}$H$_{41}$NO$_7$): | | | |
|---|---|---|---|
| | C | H | N |
| Calculated (%) | 69.67 | 7.49 | 2.54 |
| Found (%) | 69.71 | 7.45 | 2.58 |

Example 7

Synthesis of 3-(1-methyl-8-amino-6-oxaocryl)-5-(10-methyl-9-anthrylamino)-6-methyl-6-(7-amino-5-oxaheptyl)-1,2,4-trioxane expressed by the structural formula (XV)

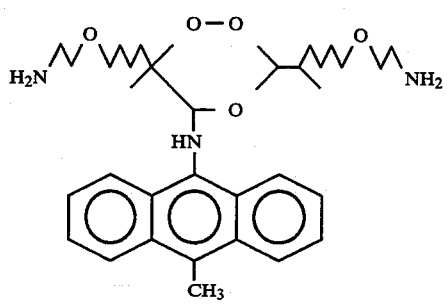

(XV)

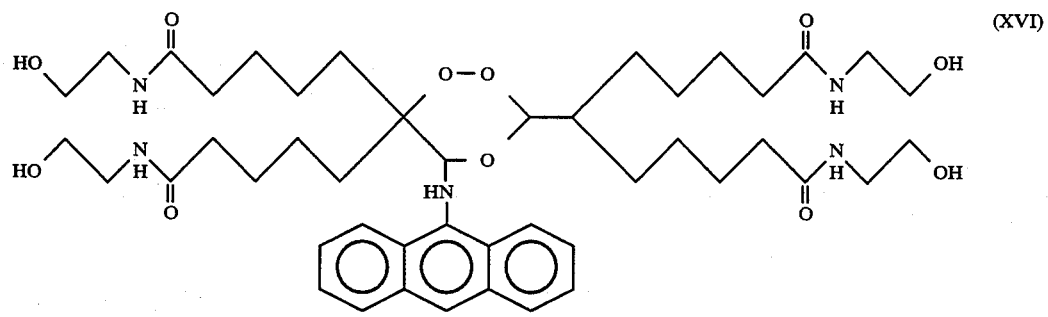

(XVI)

Under an argon atmosphere, 1.02 g (4.92 mmol) of 10-methyl-9-anthrylamine was added to a solution of dimethoxyethane—hexane (1:4) (15 ml) containing 4.87 g (15.3 mmol) of 2-methyl-9-(2-trimethylsilylethoxycarbonylaminoethoxy)-7-oxaonanal, and the resulting mixture was agitated at room temperature in a dark room overnight to effect a reaction, followed by subjecting the mixture to the reaction for one week in a moisture-free air atmosphere. The reaction liquid was concentrated. The reaction liquid was concentrated under reduced pressure, and the resulting residue was subjected to a silica gel column chromatography. By developing the same residue with hexane—ether (50:1) as an eluate, 2.87 g (3.35 mmol) of 3-[1-methyl-8-(2-trimethylsilylethoxycarbonyl) amino-6-oxaoctyl]-5-(10-methyl-9-anthrylamino)-6-methyl-6-[7-(2-trimethylsilylethoxycarbonyl) amino-5-oxaheptyl]-1,2,4-trioxane were obtained.

Into a solution of tetrahydrofuran (57 ml) containing 2.87 g (3.35 mmol) of the above-mentioned compound was added a solution of tetrahydrofuran [8.00 ml (8.00 mmol)] containing 1.0 M of tetrabutylammonium fluoride, and the resulting mixture was agitated overnight. Then a residue obtained by concentrating the reaction liquid under reduced pressure was subjected to an ethyl acetate—water extraction procedure, and its organic layer was concentrated under reduced pressure. The resulting residue was recrystallized in dichloromethane—hexane, thereby obtaining 1.54 g (2.71 mmol) of 3-(1-methyl-8-amino-6-oxaoctyl)-5-(10-methyl-9-anthrylamino)-6-methyl-6-(7-amino-5-oxaheptyl)-1,2,4-trioxane.

IR (KBr)cm$^{-1}$: 3,370, 3,300 (H—N, H2N) and 1,600 (C=C)

MS m/z : 567 (M+)

| Elemental Analysis ($C_{33}H_{49}N_3O_5$): | | | |
|---|---|---|---|
| | C | H | N |
| Calculated (%) | 69.81 | 8.70 | 7.40 |

| Elemental Analysis ($C_{33}H_{49}N_3O_5$): | | | |
|---|---|---|---|
| | C | H | N |
| Found (%) | 69.77 | 8.76 | 7.35 |

Example 8

Synthesis of 3-[bis-[4-[N-(2-hydroxyethyl) carbamoyl] butyl] methyl]-5-(9-anthrylamino)-6,6-bis[4-[N-(2-hydroxyethyl) carbamoyl] butyl]-1,2,4-trioxane expressed by the structural formula (XVI)

Under an argon atmosphere, 351 mg (1.82 mmol) of 9-anthrylamine were added to a solution of ether—hexane (1:4) (15 ml) containing 3.16 g (5.65 mmol) of bis-[4-[N-[2-(t-butyldimethylsiloxy) ethyl] carbamoyl] butyl] acetaldehyde, and the resulting mixture was agitated at room temperature in a dark room overnight to effect a reaction, followed by subjecting the mixture to the reaction for one week in a moisture-free air atmosphere. The reaction liquid was concentrated under reduced pressure, and the resulting residue was subjected to a silica gel column chromatography. By developing the same residue with hexane—ether (50:1) as an eluate, 1.39 g (1.10 mmol) of 3-[bis[4-[N-[2-(t-butyldimethylsiloxy) ethyl] carbamoyl] butyl] methyl]-5-(9-anthrylamino)-6,6-bis[4-[N-[2-(t-butyldimethylsiloxy) ethyl] carbamoyl] butyl]-1,2,4-trioxane were obtained.

Into a solution of tetrahydrofuran (37 ml) containing 1.39 g (1.10 mmol) of the above-mentioned compound was added a solution of tetrahydrofuran [5.28 ml (5.28 mmol)] containing 1.0 M of tetrabutylammonium fluoride, and the resulting mixture was agitated overnight. Then, a residue obtained by concentrating the reaction liquid under reduced pressure was subjected to an ethyl acetate—water extraction procedure, and its organic layer was concentrated under reduced pressure. The resulting residue was recrystallized in dichloromethane—hexane, thereby, obtaining 914 mg (1.05 mmol) of 3-[bis[4-[N-(2-hydroxyethyl) carbamoyl] butyl] methyl]-5-(9-anthrylamino)-6,6-bis[4-[N-(2-hydroxyethyl) carbamoyl] butyl]-1,2,4-trioxane.

IR (KBr)cm$^{-1}$ : 3,380, 3,300 (H—N, H—O), 1,660 (O=C) and 1,605 (C=C)

MS m/z : 867 (M+)

| Elemental Analysis ($C_{46}H_{69}N_5O_{11}$): | | | |
|---|---|---|---|
| | C | H | N |
| Calculated (%) | 63.65 | 8.01 | 8.07 |
| Found (%) | 63.69 | 8.07 | 8.03 |

Example 9

Synthesis of 3-(1-methyl-5-mercaptopentyl)-5-(2-anthrylamino)-6-methyl-6-(4-mercaptobityl) -1,2,4-trioxane expressed by the structural formula (XVII)

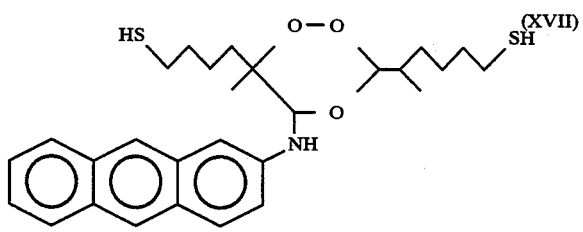

Under an argon atmosphere, 1.28 g (6.62 mmol) of 2-anthrylamine was added to a solution of hexane (13 ml) containing 3.48 g (18.5 mmol) of 2-methyl-6-(s-acetylmercapto) hexanal, and the resulting mixture was agitated at room temperature in a dark room overnight to effect a reaction, followed by subjecting the mixture to the reaction for one week in a moisture-free air atmosphere. The reaction liquid was concentrated under reduced pressure, and the resulting residue was subjected to a silica gel column chromatography. By developing the same residue with hexane—ether (50:1) as an eluate, 2.05 g (3.51 mmol) of 3-[1-methyl-5-(s-acetylmercapto) pentyl]-5-(2-anthrylamino)-6-methyl-6-[4-(s-acetylmercaptobutyl)]-1,2,4-trioxane was obtained.

Into a solution of methanol (42 ml) containing 2.05 g (3.51 mmol) of the above-mentioned compound, 970 mg (7.02 mmol) of potassium carbonate were added at 0° C., and agitated for 30 minutes. On the reaction liquid, an ether—water extraction was carried out, and its organic layer was concentrated under reduced pressure. The resulting residue was recrystallized in dichloromethane—hexane, thereby obtaining 1.51 g (3.02 mmol)of 3-(1-methyl-5-acrcaptopentyl)-5-(2-anthrylamino) -6-(4-mercaptobutyl)-1.2.4-trioxane.

IR (KBr)cm$^{-1}$: 3,375 (H—N) and 1,610 (C=C)
MS m/z : 499 (M+)

| Elemental Analysis (C$_{28}$H$_{37}$NO$_3$S$_2$): | | | |
|---|---|---|---|
| | C | H | N |
| Calculated (%) | 69.87 | 7.49 | 2.54 |
| Found (%) | 69.71 | 7.45 | 2.58 |

Example 10

As to a dimethylsulfoxide solution containing 10$^{-3}$ M of 3-(1-methyl-6-carboxyhexyl)-5-(9-anthrylamino)-6-methyl-6-(5-carboxypentyl) -1,2,4-trioxane synthesized in the above-described example 6 as a measurement compound, 100 μl of the same solution was injected into a cell filled with 900 μl of a base-containing solvent in a chemiluminescence measurement apparatus, and just after the injection, a quantity of emission for 10 seconds was measured. At that time, adimethylsulfoxide solution containing 0.05M of potassium t-butoxide was used as abase-containing organic solvent, and an aqueous solution containing 10M of sodium hydroxide was used as an aqueous solvent. The measurement results thereof are shown in Table 2. In addition, found count numbers in Table 2 are relative values of "no unit".

Comparative Example 2

The same measurement test as in the above-mentioned example 10 was carried out by use of 5-(9-anthrylamino)-3-isopropyl-6,6-dimethyl-1,2,4-trioxane, in place of 3 -(1-methyl-6-carboxyhexyl)-5-(9-anthrylamino)-6-(5-carboxypentyl) -1,2,4-trioxane measured in the above-mentioned example 10. The results thereof are shown in Table 2. In addition, found count numbers in Table 2 are also relative values of "no unit".

TABLE 2

| Example | Organic solvent | Aqueous Solvent |
|---|---|---|
| Example 10 | 2.51 × 10$^5$ | 2.39 × 10$^5$ |
| Comparative Example 2 | 2.14 × 10$^5$ | 5.31 × 10$^3$ |

EFFECT AND MERIT OF INVENTION

A. The novel trioxane derivatives of this invention have an effect that the use of trioxane derivatives as a chemiluminosity is enlarged, because they also emit the same level amount of light in an aqueous solvent system as in an organic solvent system.

B. The novel trioxane derivatives of this invention have an effect that the use for the detection of various diagnostics for instance detections of virus, hormones, hepatitis and cancer marker, or the application for the biochemical reaction of cell, blood, etc. is enlarged together with the effect of A as described above, because they have substituents capable of bonding with protein, nucleic acid, etc.

What is claimed is:

1. Trioxane derivatives represented by the formula (1):

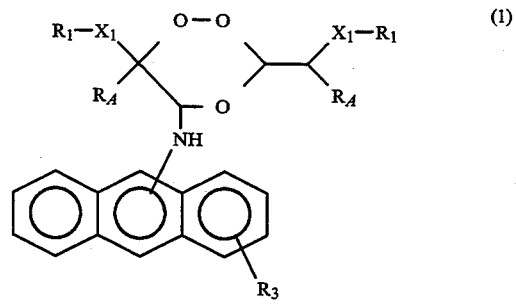

wherein RA is methyl or R$_2$—X$_2$—, and wherein X$_1$ and X$_2$ represent independently —(CH$_2$)$_m$—, —(CH$_2$-)$_m$—(O—Z)$_n$—or

—(CH$_2$)$_m$—CNH—(CH$_2$)$_n$—, where m and n represent an integer of from 1–10 and Z represents a lower alkylene group, R$_1$ and R$_2$ represent independently carboxyl, amino, hydroxyl or mercapto; and R$_3$ represents hydrogen or methyl.

2. Trioxane derivatives represented by the formula (2):

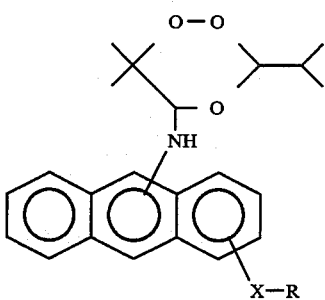
(2)

wherein X represents —$(CH_2)_m$—, —$(CH_2)_m$—$(O$—$Z)_n$—or

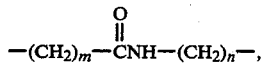

where m and n represent an integer of from 1–10 and Z represents a lower alkylene group, and R represents carboxyl, amino, hydroxyl or mercapto.

3. A method for producing chemiluminescence, wherein the chemiluminescence is effected by mixing trioxane derivative represented by the formula (1):

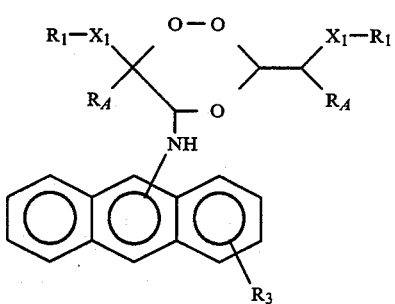
(1)

wherein RA is methyl or $R_2$—$X_2$—, and wherein $X_1$ and $X_2$ represent independently —$(CH_2)_m$—, —$(CH_2)_m$—$(O$—$Z)_n$—or $$-(CH_2)_m-\overset{\overset{O}{\|}}{C}NH-(CH_2)_n-,$$

where m and n represent an integer of from 1–10 and Z represents a lower alkylene, $R_1$ and $R_2$ represent independently carboxyl, amino, hydroxyl or mercapto; and $R_3$ represents hydrogen or methyl; and a base.

4. A method for producing chemiluminescence, wherein the chemiluminescence is effected by mixing trioxane derivative represented by the formula (2):

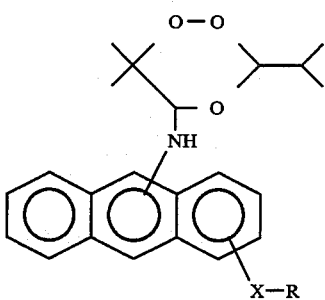
(2)

wherein X represents —$(CH_2)_m$—, —$(CH_2)_m$—$(O$—$Z)_n$—or

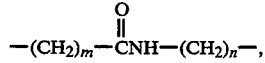

where m and n represent an integer of from 1–10 and Z represents a lower alkylene group, and R represents carboxyl, amino, hydroxdyl or mercapto; and R represents carboxyl, amino, hydroxyl or mercapto; and a base.

* * * * *